United States Patent
Frederickson et al.

(10) Patent No.: US 8,784,363 B2
(45) Date of Patent: Jul. 22, 2014

(54) MICRONEEDLE ARRAY APPLICATOR DEVICE AND METHOD OF ARRAY APPLICATION

(75) Inventors: Franklyn L. Frederickson, White Bear Lake, MN (US); Michael D. Johnson, College Station, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 1004 days.

(21) Appl. No.: 11/993,137

(22) PCT Filed: Jun. 23, 2006

(86) PCT No.: PCT/US2006/024671
§ 371 (c)(1),
(2), (4) Date: Dec. 19, 2007

(87) PCT Pub. No.: WO2007/002521
PCT Pub. Date: Jan. 4, 2007

(65) Prior Publication Data
US 2010/0222743 A1  Sep. 2, 2010

Related U.S. Application Data

(60) Provisional application No. 60/694,447, filed on Jun. 27, 2005, provisional application No. 60/746,298, filed on May 3, 2006.

(51) Int. Cl.
*A61B 17/20* (2006.01)
(52) U.S. Cl.
USPC ............................................... 604/46
(58) Field of Classification Search
USPC ............... 604/93.01, 115, 156, 289, 46–47
See application file for complete search history.

(56) References Cited

U.S. PATENT DOCUMENTS

| | | | |
|---|---|---|---|
| 3,034,507 A | 5/1962 | McConnell et al. |
| 3,072,122 A | 1/1963 | Rosenthal |
| 3,123,212 A | 3/1964 | Taylor et al. |
| 3,136,314 A | 6/1964 | Kravitz |

(Continued)

FOREIGN PATENT DOCUMENTS

| | | |
|---|---|---|
| EP | 407063 | 1/1991 |
| GB | 1080986 | 8/1967 |

(Continued)

OTHER PUBLICATIONS

Daddona. Current Opinion in Drug Discovery and Development 1999 2(2);168-171.

(Continued)

*Primary Examiner* — Laura Bouchelle
*Assistant Examiner* — Melissa A Snyder (57) ABSTRACT

An applicator device (20) including a housing (22), an impactor (62) for impacting a microneedle array and accelerating the microneedle array toward the target site, wherein the impactor is capable of moving along an arcuate path to move the microneedle array toward the target site. Also, an applicator device including a housing, a patch applicator pivotally supported by the housing, and a torsion spring. The patch applicator has a retaining portion (40) and a patch contacting portion (70), and the patch contacting portion is capable of moving along a substantially arcuate path between a first position and a second position. The torsion spring is capable of biasing the patch applicator relative to the housing.

18 Claims, 7 Drawing Sheets

(56) References Cited

U.S. PATENT DOCUMENTS

| | | |
|---|---|---|
| RE25,637 E | 9/1964 | Kravitz et al. |
| 3,221,740 A | 12/1965 | Rosenthal |
| 3,246,647 A | 4/1966 | Taylor et al. |
| 3,322,121 A | 5/1967 | Banker |
| 3,466,131 A | 9/1969 | Arcudi |
| 3,510,933 A | 5/1970 | Taylor et al. |
| 3,512,520 A | 5/1970 | Cowan |
| 3,596,660 A | 8/1971 | Melone |
| 3,675,766 A | 7/1972 | Rosenthal |
| 3,678,150 A | 7/1972 | Szumski et al. |
| 3,688,764 A | 9/1972 | Reed et al. |
| 3,905,371 A | 9/1975 | Stickl et al. |
| 3,964,482 A | 6/1976 | Gerstel et al. |
| 4,109,655 A | 8/1978 | Chacornac |
| 4,237,906 A | 12/1980 | Havstad et al. |
| 4,304,241 A | 12/1981 | Brennan |
| 4,360,016 A | 11/1982 | Sarrine |
| 4,453,926 A | 6/1984 | Galy |
| 4,503,856 A | 3/1985 | Cornell et al. |
| 4,517,978 A | 5/1985 | Levin et al. |
| 4,637,403 A | 1/1987 | Garcia et al. |
| 4,858,607 A | 8/1989 | Jordan et al. |
| 4,869,249 A | 9/1989 | Crossman et al. |
| 4,920,977 A | 5/1990 | Haynes |
| 4,924,879 A | 5/1990 | O'Brien |
| 5,250,023 A | 10/1993 | Lee et al. |
| 5,318,584 A | 6/1994 | Lange et al. |
| 5,368,047 A | 11/1994 | Suzuki et al. |
| 5,402,798 A | 4/1995 | Swierczek et al. |
| 5,487,726 A | 1/1996 | Rabenau et al. |
| 5,611,806 A | 3/1997 | Jang |
| 5,879,326 A | 3/1999 | Godshall et al. |
| 5,983,136 A | 11/1999 | Kamen |
| 6,050,988 A | 4/2000 | Zuck |
| 6,091,975 A | 7/2000 | Daddona et al. |
| 6,132,755 A | 10/2000 | Eicher et al. |
| 6,256,533 B1 | 7/2001 | Yuzhakov et al. |
| 6,293,925 B1 | 9/2001 | Safabash et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,379,324 B1 | 4/2002 | Gartstein et al. |
| 6,440,096 B1 | 8/2002 | Lastovich et al. |
| 6,454,755 B1 | 9/2002 | Godshall |
| 6,503,231 B1 | 1/2003 | Prausnitz et al. |
| 6,532,386 B2 | 3/2003 | Sun et al. |
| 6,537,242 B1 | 3/2003 | Palmer |
| 6,589,202 B1 | 7/2003 | Powell |
| 6,591,124 B2 | 7/2003 | Sherman et al. |
| 6,595,947 B1 | 7/2003 | Mikszta et al. |
| 6,603,998 B1 | 8/2003 | King et al. |
| 6,623,457 B1 | 9/2003 | Rosenberg |
| 6,713,291 B2 | 3/2004 | King et al. |
| 6,743,211 B1 | 6/2004 | Prausnitz et al. |
| 6,780,171 B2 * | 8/2004 | Gabel et al. .................. 604/181 |
| 6,797,276 B1 | 9/2004 | Glenn et al. |
| 6,855,131 B2 | 2/2005 | Trautman et al. |
| 6,881,203 B2 | 4/2005 | Delmore et al. |
| 6,890,319 B1 | 5/2005 | Crocker |
| 6,908,453 B2 | 6/2005 | Fleming et al. |
| 6,931,277 B1 | 8/2005 | Yuzhakov et al. |
| 2002/0032415 A1 | 3/2002 | Trautman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0095134 A1 | 7/2002 | Pettis et al. |
| 2002/0111600 A1 | 8/2002 | Cormier et al. |
| 2002/0123675 A1 | 9/2002 | Trautman et al. |
| 2002/0138049 A1 | 9/2002 | Allen et al. |
| 2002/0169416 A1 | 11/2002 | Gonnelli et al. |
| 2002/0177858 A1 | 11/2002 | Sherman et al. |
| 2002/0188245 A1 | 12/2002 | Martin et al. |
| 2002/0198509 A1 | 12/2002 | Mikszta et al. |
| 2003/0045837 A1 | 3/2003 | Delmore et al. |
| 2003/0050602 A1 | 3/2003 | Pettis et al. |
| 2003/0083641 A1 | 5/2003 | Angel et al. |
| 2003/0135158 A1 | 7/2003 | Gonnelli |
| 2003/0181863 A1 | 9/2003 | Ackley et al. |
| 2003/0199812 A1 | 10/2003 | Rosenberg |
| 2003/0208167 A1 | 11/2003 | Prausnitz et al. |
| 2004/0049150 A1 | 3/2004 | Dalton et al. |
| 2004/0064087 A1 * | 4/2004 | Lastovich et al. ............... 604/46 |
| 2004/0077994 A1 | 4/2004 | Lastovich et al. |
| 2004/0138612 A1 | 7/2004 | Shermer et al. |
| 2004/0176732 A1 | 9/2004 | Frazier et al. |
| 2004/0181203 A1 | 9/2004 | Cormier et al. |
| 2005/0025778 A1 | 2/2005 | Cormier et al. |
| 2005/0027242 A1 | 2/2005 | Gabel et al. |
| 2005/0065463 A1 | 3/2005 | Tobinaga et al. |
| 2005/0065466 A1 * | 3/2005 | Vedrine .................... 604/93.01 |
| 2005/0065472 A1 | 3/2005 | Cindrich et al. |
| 2005/0096586 A1 | 5/2005 | Trautman et al. |
| 2005/0106226 A1 | 5/2005 | Cormier et al. |
| 2005/0137525 A1 | 6/2005 | Wang et al. |
| 2005/0261631 A1 | 11/2005 | Clarke et al. |

FOREIGN PATENT DOCUMENTS

| | | | |
|---|---|---|---|
| GB | 2064329 | 6/1981 | |
| GB | 2221394 | 2/1990 | |
| WO | WO 96/10630 | 4/1996 | |
| WO | WO 01/36037 | 5/2001 | |
| WO | WO 2004/009172 | 1/2004 | |
| WO | WO2004/098684 | 11/2004 | ............ A61M 5/142 |
| WO | WO 2005/051455 | 6/2005 | |
| WO | WO 2005/051476 | 6/2005 | |
| WO | WO 2005/065765 | 7/2005 | |
| WO | WO 2005/123173 | 12/2005 | |

OTHER PUBLICATIONS

Kaushik et al. Anesthesia Analg., 2001, 92, 502-504.
Henry et al. J. Pharm.Sci., 1998, 87,8,922-925.
McAllister et al. Annual Review of Biomedical Engineering, 2000, 2, 289-313.
McAllister et al. Proceed. Int'l. Symp. Control Release of Bioactive Material, 26, (1999), CRS, 192-193.

* cited by examiner

MICRONEEDLE ARRAY APPLICATOR DEVICE AND METHOD OF ARRAY APPLICATION

CROSS REFERENCE TO RELATED APPLICATIONS

This application is a national stage filing under 35 U.S.C. 371 of PCT/US2006/024671, filed Jun. 23, 2006, which claims priority to U.S. Application No. 60/694,447, filed Jun. 27, 2005 and U.S. Application No. 60/746,298, filed May 3, 2006, the disclosure of which is incorporated by reference in its/their entirety herein.

FIELD

The present invention relates to microneedle array applicators and methods of application of microneedle arrays.

BACKGROUND

Only a limited number of molecules with demonstrated therapeutic value can be transported through the skin via unassisted or passive transdermal drug delivery. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through the stratum corneum and into the tissues below. Microneedles can be delivered using a patch that carries the microneedle array, which can facilitate delivery of therapeutic agents and other substances.

Microneedle arrays and patches can be deployed with an applicator device capable of being used a number of different times. The microneedle arrays and patches are generally used once and then discarded. The applicator devices can be repeatedly reloaded with new microneedle arrays and patches.

The present invention provides an alternative microneedle array applicator device.

BRIEF SUMMARY

In a first aspect of the present invention, a microneedle array application device includes a housing and an impactor. The housing has a skin-contacting face that defines an opening that can be positioned at a target site. The impactor is capable of impacting a microneedle array and accelerating the microneedle array toward the target site. The impactor is further capable of moving along an arcuate path to move the microneedle array toward the target site.

In another aspect of the present invention, a microneedle array application device includes a housing having a surface-contacting face with an opening and a drive member having a length extending from a fixed end attached to the housing to a movable end. The drive member is bendable along its length and the movable end of the drive member is configured so as to be able to contact and propel a microneedle array. In one embodiment, the drive member comprises a leaf spring.

In another aspect of the present invention, an applicator device includes a housing, an impactor pivotally supported by the housing, and a torsion spring. The impactor has an impacting portion that is capable of moving along a substantially arcuate path between a first position and a second position. The torsion spring is capable of biasing the impactor relative to the housing.

In another aspect of the present invention, a microneedle application device includes a housing having a skin-contacting face. A recess is defined along the skin-contacting face of the housing, and the recess has a bottom portion. An opening is defined in the bottom portion of the recess, and the opening can be positioned over a target site. At least one retaining surface is disposed along the bottom portion of the recess and adjacent to the opening, for holding a patch carrying a microneedle array prior to application at the target site. The retaining surface is generally parallel to the bottom portion of the recess, and the microneedle array can be aligned below the opening.

In another aspect of the present invention, a microneedle array application device includes a housing and an impactor. The housing has a skin-contacting face that defines an opening that can be positioned at a target site. The impactor is capable of impacting a microneedle array and accelerating the microneedle array toward the target site. The impactor comprises a magnet suitable for releasably retaining a magnetic microneedle patch.

In another aspect of the present invention, a method of microneedle array application includes providing a microneedle application device capable of accelerating a microneedle array toward a target site, mounting the microneedle array on the microneedle array application device, and moving the microneedle array toward the target site along a substantially arcuate path.

In another aspect of the present invention, a method of microneedle, array application includes providing a microneedle application device capable of bringing a microneedle array toward a target site, mounting the microneedle array on the microneedle array application device, and moving the impactor along a substantially arcuate path to bring the microneedle array into contact with the target site.

The above summary is not intended to describe each disclosed embodiment or every implementation of the present invention. The figures and the detailed description, which follow, more particularly exemplify illustrative embodiments.

While the above-identified drawing figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers have been used throughout the figures to denote like parts.

DETAILED DESCRIPTION

Microneedle arrays can be used for transdermal or intradermal delivery of molecules, and in particular may have utility for the delivery of large molecules that are ordinarily difficult to deliver by passive transdermal delivery. In some instances, the microneedle arrays may be applied as part of a microneedle device which, for example, may be in the form of a patch designed to adhere to skin and help keep the array in intimate contact with the skin. As used herein, "array" refers to the medical devices described herein that include one or more structures capable of piercing the stratum corneum to facilitate the transdermal delivery of therapeutic agents or the sampling of fluids through or to the skin. "Microstructure," "microneedle" or "microarray" refers to the specific microscopic structures associated with the array that are capable of piercing the stratum corneum to facilitate the transdermal delivery of therapeutic agents or the sampling of fluids through the skin. By way of example, microstructures can include needle or needle-like structures as well as other structures capable of piercing the stratum corneum. Microneedle arrays can be deployed using an applicator device that moves microneedle arrays into contact with a target location, such as a location on a patient's skin.

Figure 1:
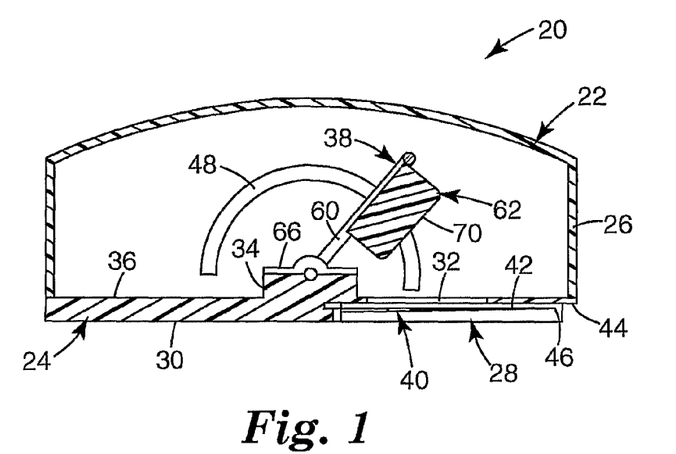
FIG. 1 is a cross-sectional view of an applicator device.

FIG. 1 is a cross-sectional view of an applicator device 20 having a housing 22 that includes a base 24 and an upper cover structure 26. The base 24 is generally rectangular in shape, and has a recess 28 located on a bottom face 30 thereof. A generally circular opening 32 is defined in the recess 28 of the base 24. A raised portion 34 is formed on an upper face 36 of the base 24 for holding a patch accelerating or patch applicator assembly 38.

A mounting structure or retaining portion of the applicator device 20 is formed by a pair of retainers 40, also referred to as a first retainer and a second retainer, connected to the base 24 (only one retainer 40 is visible in FIG. 1). The retainer members 40 are generally elongate and each have a substantially flat upper surface 42 that is generally parallel to and facing a bottom portion 44 of the recess 28, and is spaced from the bottom face 30 (i.e., the skin-contacting face) of the base 24. The pair of retainer members 40 are located on opposite sides of the opening 32 and are connected to the base 24 at one side of the recess 28. The retainer members 40 define an opening 46 at one end for accepting patches between the retainer members 40 and the bottom portion 44 of the recess 28. The upper surfaces 42 of the retainer members 40 may be non-stick or release surfaces. A non-stick or release surface can be achieved, for example, by a non-stick or release coating applied to the upper surfaces 42. The non-stick or release coating can be selected according to the desired use of the applicator device 20. For instance, a release coating, such as a low surface energy silicone, fluoropolymer, or fluoro-silicone release coating, can be selected based upon the adhesives used with patches applied using the patch application device 20. In further embodiments, a blade or other cutting means can be provided as part of the mounting structure, for separating portions of items from patches mounted on the applicator.

The upper cover structure 26 is connected to the base 24 at or near a perimeter of the base 24. The upper cover structure 26 is shaped to fit on the base 24, and defines a volume, which is selected to provide space for the patch accelerating assembly 38. In some embodiments, the housing 22 may also provide space for storing patches (e.g., a roll of patches) for eventual deployment by the applicator device 20. A slot 48 is defined in a side portion of the upper cover structure 26. In the embodiment shown in FIG. 1, the slot 48 is arcuate in shape and generally resembles a half circle, with the open portion of the half circle facing the base 24 of the housing 22.

Both the base 24 and the upper cover structure 26 can be formed of a polymer material.

Figure 2:
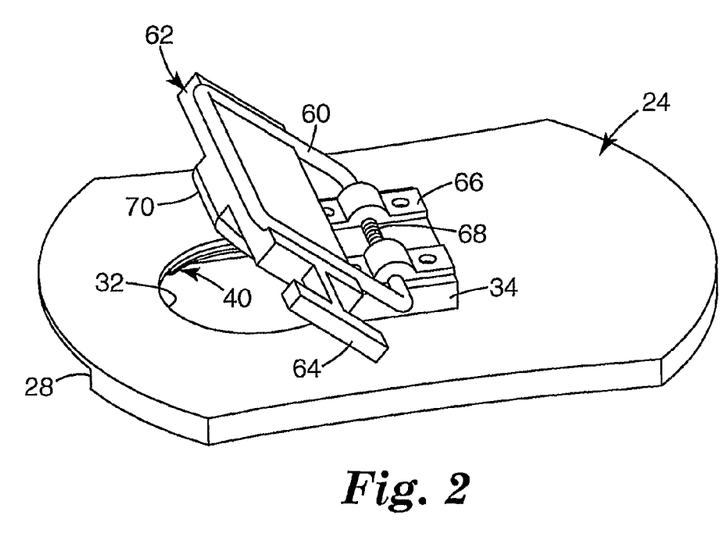
FIG. 2 is a perspective view of a portion of the applicator device of FIG. 1.
Figure 5A:
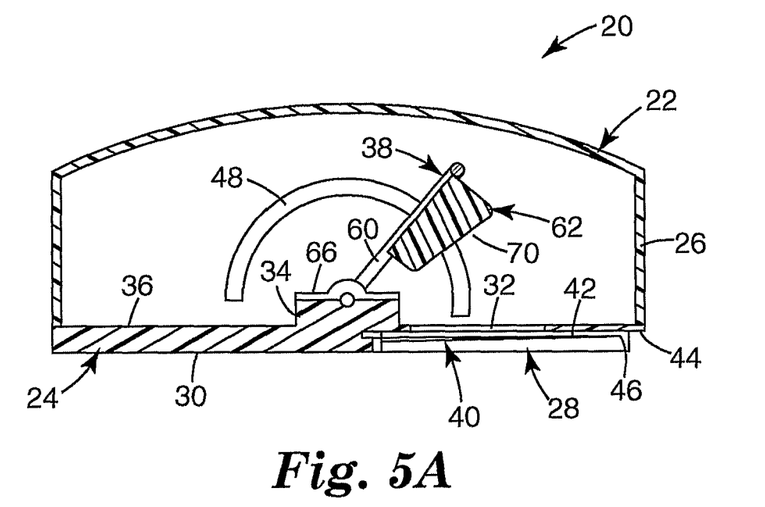
FIG. 5A is a detailed view the patch contacting surface of one embodiment of an applicator device.
Figure 5B:
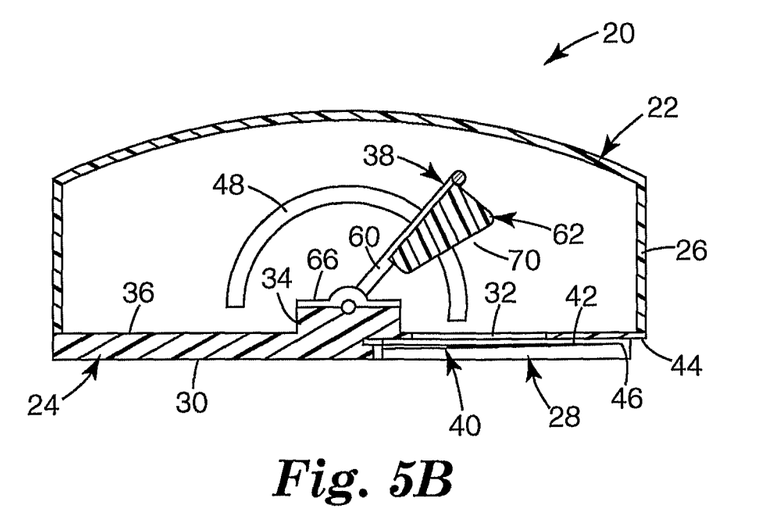
FIG. 5B is a detailed view the patch contacting surface of another embodiment of an applicator device.

FIG. 2 is a perspective view of a portion of the applicator device 20 with the upper cover portion 26 omitted to show interior portions of the device 20. As shown in FIG. 2, the patch acceleration assembly 38 includes a frame member 60, an impactor 62, a handle 64, a bracket 66, and a torsion spring 68. The torsion spring 68 serves as a drive member to bias the impactor relative to the housing. The bracket 66 is mounted to the raised portion 34 of the base 24 of the housing 22 and pivotally retains the frame member 60. In some instances the bracket 66 may be directly affixed to the base 24, for example, if the base has sufficient thickness to allow for placement of the torsion spring 68. The frame member 60 can be a wire formed as a rectangular loop. The impactor 62 is attached to the frame member 60 opposite the bracket 66, and is the portion of the patch acceleration assembly 38 that interfaces with a patch to move it (i.e., to accelerate it), that is, it is the patch contacting portion of the device. The impactor 62 has a patch contacting surface 70 that is configured according to characteristics of a desired application, for instance, based upon the shape of a patch to be applied. In the embodiment shown in FIG. 1, the patch contacting surface 70 is configured so that it is generally parallel to and aligned with the frame member 60. Furthermore, it will be generally aligned with the bottom face 30 of the device 20 when fully deployed. It other embodiments, the patch contacting surface 70 may be configured so that it is at another angle with respect to the frame member 60, and with respect to the bottom face 30 of the device 20 when fully deployed. Other such angles are shown in FIGS. 5A, B depicting a portion of devices having alternative patch contacting surfaces. In one embodiment, it may be desirable for the patch contacting surface 70 to be aligned so as to form an angle of between 4 and 15 degrees with the plane of the frame member. In one aspect, the angle of the patch contacting surface 70 may be selected so that it is aligned with the back of the a patch resting on retaining members 40 when the patch contacting surface 70 contacts the patch. The impactor 62 can be formed of a polymer material. The handle 64 extends from the impactor 62, and can be integrally formed with the impactor 62. The handle 64 is arranged to protrude through the slot 48 in the upper cover structure 26 of the housing 22, allowing the impactor 62 position to be manipulated from outside the housing 22. It should be understood that FIG. 1 simply represents one configuration for manipulating the patch acceleration assembly 38. For example, a slot may be provided on the upper cover portion 26, thereby allowing the handle 64 or any other suitable actuation protrusion to protrude through the upper cover portion 26. Furthermore, the method for manipulating the patch acceleration assembly 38 need not be by means of a direct mechanical connection. For example, various linkages or gears may be provided such that a button or knob on the exterior of the housing 22 may be pressed or turned to manipulate the patch acceleration assembly 38. In a further example, the patch acceleration assembly 38 may be moved by a motor or solenoid that is electrically controlled by a button or knob on the exterior of the housing 22.

The torsion spring 68 biases the frame 60 of the patch acceleration assembly 38 relative to the base 24 of the housing 22. The torsion spring 68 can be a conventional coiled spring steel torsion spring. By default, the torsion spring 68 biases the frame 60, and therefore also the impactor 62, toward the opening 32 in the base 24 of the housing 22. In a substantially de-energized state, the impactor is at rest and positioned near the opening 32 in the base 24 of the housing 22. By moving the handle 64 to position the impactor 62 away from the opening, along an arcuate path that can be defined by movement of the handle 64 along the slot 48 in the upper cover structure 26 of the housing 22, an operator can store potential energy in the torsion spring 68. Energy stored in the torsion spring 68 can be used to accelerate the impactor 62 toward a patch and also to accelerate a patch that has contacted the impactor 62. The amount of energy stored in the torsion spring 68 will vary depending on the amount of displacement of the impactor 62 away from the opening 32 and along the arcuate path. The appropriate torsion spring constant will depend upon a number of parameters, including the mass of the patch acceleration assembly, the mass of the patch, the arc length through which the patch acceleration assembly travels, and the desired speed of the patch on impact with a surface. The torsion spring constant will often be more than about 0.5 Newton*mm/degree and sometimes more than about 2.0 Newton*mm/degree. The torsion spring constant will often be less than about 5.0 Newton*mm/degree and sometimes less than about 4.0 Newton*mm/degree. The impactor 62 can be held at various points along the arcuate path either manually or, in some embodiments, with holding means (not shown) that engage and temporarily secure the handle 64 along the slot 48 in the upper cover structure 26 of the housing 22. In further embodiments, demarcations or other indicators (e.g., a force readout display) can be provided for indicating the levels of force associated with particular degrees of displacement of the impactor 62 along the arcuate path.

The range of angular travel of the patch acceleration assembly will often be less than about 170 degrees and sometimes less than about 110 degrees. The range of angular travel of the patch acceleration assembly will often be more than about 10 degrees and sometimes more than about 60 degrees. The mass of the patch acceleration assembly will often be more than about 1 gram and sometimes more than about 5 grams. The mass of the patch acceleration assembly will often be less than about 100 grams and sometimes less than about 30 grams.

Figure 3:
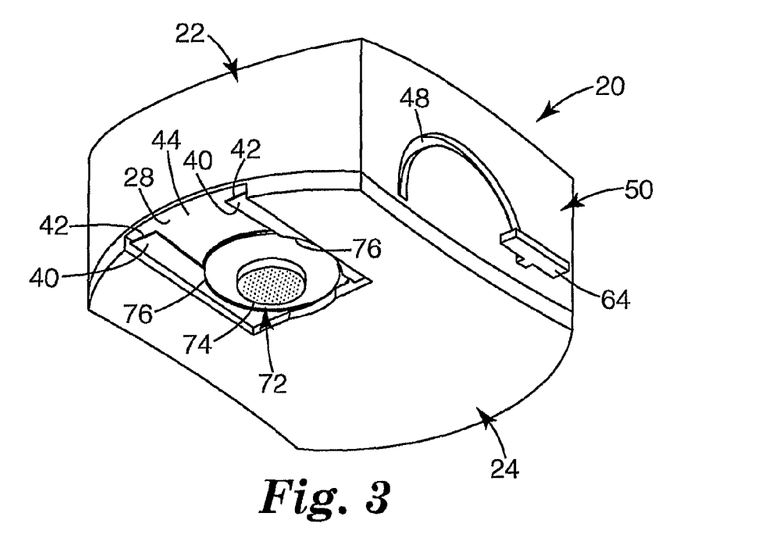
FIG. 3 is a perspective view of a patch mounted on the applicator device of FIGS. 1 and 2.

FIG. 3 is a perspective view of a patch 72 (e.g., a patch 72 carrying a microneedle array 74) mounted on the applicator device 20. The patch 72 is disposed between the retainer members 40 and the bottom portion 44 of the recess 28 in the base 24 of the housing 22. The microneedle array 74 faces away from the opening 32 in the base 24 of the housing 22. The patch 72, which may have adhesive surrounding the microneedle array 74 on the surface facing away from the patch application device 20, contacts the upper surfaces 42 of the retainer members 40, but is generally not adhered firmly to the retainer members 40 due to the release character of the upper surfaces 42. In a fully mounted position, as shown in FIG. 3, microneedle array carried on the patch 72 is generally aligned relative to the opening 32 in the base 24 of the housing 22 (the opening 32 is not visible in FIG. 3).

The retainer members 40 have cutaway portions 76 that provide an enlarged, partially circular open region that is generally aligned with the opening 32 on the bottom portion 44 of the recess 28 of the base 24 of the housing 22. The wider, open region defined by the cutaway portions 76 facilitates patch application by reducing the amount of deflection of the patch 72 required during deployment to move the patch 72 from a mounted position on the applicator device 20 to a target location. Such cutaway portions 76 are optional and may be unnecessary if, for example, the patch has a generally rectangular shape.

Figure 4:
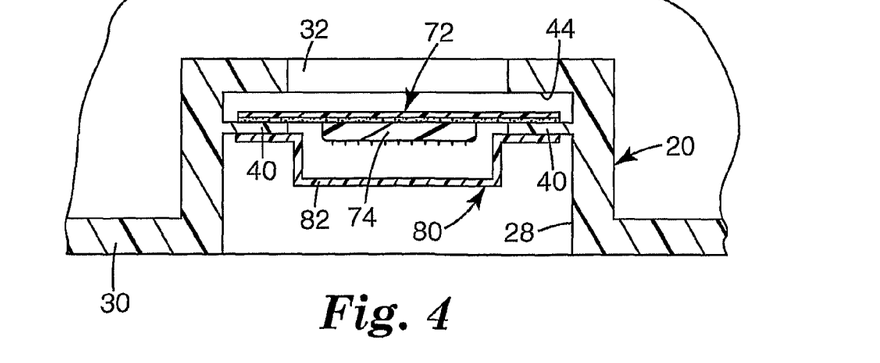
FIG. 4 is a partial cross-sectional view of a microneedle cartridge mounted on the applicator device of FIGS. 1-3.

FIG. 4 is a partial cross-sectional view of a microneedle array cartridge 80, having a patch 72 and a cover 82, mounted on the applicator device 20. Mounting the patch 72 on the applicator device 20 includes the following steps. The cartridge 80 is partially slid onto the retainer members 40. Then the cartridge 80 is slid further along the retainer members 40, simultaneously separating the cover 82 from the patch 72, until the patch 72 is fully mounted on the applicator device 20 (e.g., such that the microneedle array 74 is aligned with the opening 32 defined in the bottom portion 44 of the recess 28). The cover 82 is removed from (i.e., separated from) the patch 72 to uncover and expose the microneedle array 74 prior to microneedle deployment.

It should be recognized that the patch mounting structure shown in FIGS. 3 and 4 is provided by way of example, and not limitation. In further embodiments, other means of mounting a patch on the applicator device 20 can be used, and the design of the mounting structure is generally independent of the design of other components of the applicator device 20. For instance, in further embodiments, one or more patches can be stored inside the housing 22 prior to application, and then dispensed for application to a target site. The microneedle array 74 of the patch 72 can be deployed as follows. An operator "loads" or "energizes" the patch accelerating assembly 38 using the handle 64, to store potential energy in the torsion spring 68, by moving the impactor 62 and frame 60 along the arcuate path. The operator can "load" the patch accelerating assembly 38 either before or after the patch 72 is mounted to the device 20. The amount of energy stored in the torsion spring 68 can be selected based on characteristics of the desired patch application site, and may vary for different target sites, or may vary for different patches. Storing different amounts of energy in the torsion spring 68 permits adjustment of an acceleration rate of a patch moved by the patch accelerating assembly 38.

The applicator device 20 is also positioned against an application surface, and the opening 32 is positioned relative to a target site for patch delivery. Suitable sites for microneedle patch application on a patient's skin will vary, and the operator must select a suitable position and orientation of the applicator device 20. When the patch accelerating assembly 38 is energized, the patch 72 is fully mounted to the applicator device 20, and the device 20 is positioned relative to the target location, the operator then actuates the impactor 62 by releasing the energy stored in the torsion spring 68, which moves the impactor 62 toward the patch 72 along an arcuate path, which can correspond to the arcuate path defined by the slot 48 in the housing 22. The patch contacting surface 70 of the impactor 62 then contacts the patch 72 to transfer energy to the patch 72 and accelerate it toward the target site. Release of the stored energy may be by any suitable means, such as by pressing a button or turning a knob to release a latch or other locking mechanism and thereby allowing the patch accelerating assembly 38 to accelerate the patch 72 toward the target site. As shown, the arcuate path defined by the slot 48 is a portion (or arc) of a circle. It should be understood that in other embodiments the impactor may move along any type of arcuate (i.e., curved) path. Furthermore the path may be substantially arcuate, that is, although predominately curved, there may be small portions of the path which are not curved.

In one embodiment (not shown), the patch may be directly affixed or otherwise releasably held by the patch acceleration assembly. For example, the patch may be releasably held to the impactor through magnetic attraction. The impactor may comprise a magnet and the patch may comprise a metal capable of magnetic attraction. The impactor, for example, may be a permanent magnet or an electromagnet and the patch backing may comprise a metal that can be magnetically attracted. For example, a thin layer of ferrous foil may be incorporated into the patch backing. Such a magnetic attraction can allow the patch to be held to the impactor until the patch contacts the skin. The adhesion between the patch and the skin can then be sufficient to allow the patch acceleration assembly, and thus the applicator, to be removed from the patch while allowing the patch to remain in place on the skin. The adhesive force between the patch and the skin is typically more than the magnetic, attractive force between the patch and the impactor. In some instances the adhesive force between patch and skin may be more than about twice as much as the magnetic, attractive force between patch and impactor. The appropriate amount of magnetic interaction may be readily determined, and will depend on a number of factors, including the magnitude of the adhesive force between the patch and the skin, the design of the applicator and its method of removal from the patch once the patch is applied to the skin. Alternatively, the patch may incorporate a magnet and the impactor can be made of a magnetic material, such as a steel leaf spring. Releasable magnetic attachment may be used with any of the hereinbefore or hereinafter describe embodiments, as well as with other embodiments of applicators, such as those described in United States Patent Application Publication 2002-0087182 and International Patent Publication WO 05/123173, the disclosures of which are herein incorporated by reference.

Other releasable attachments, such as a weak adhesive bond, a snap-fit mechanism or a hook-and-loop attachment may also be suitable to connect patch to impactor. In still another embodiment, the patch may be releasably attached to a portion of the holding mechanism. For example, the impactor may be an elongated drive member, such as a leaf spring having an opening or hole in its movable end. The patch may have a stub or other protrusion extending from its back surface that can be placed through the opening or hole in the leaf spring and gripped by the holding mechanism. The leaf spring will then also be held in place in a cocked position, as it will be pinned between the patch and the holding mechanism. Release of the patch from its attachment to the holding mechanism and release of the leaf spring from its cocked position may then occur simultaneously by activating the trigger. In one embodiment, a single use, disposable unit may be provided with the patch accelerating assembly 38 already in an energized position, so that the device may be positioned and fired with the press of a button.

The patch 72 can be moved toward the target site along an at least partially arcuate path, such as when the patch 72 is moved in contact with the impactor 62 as the impactor 62 moves along its arcuate path. The patch 72 could also move linearly toward the target site after contacting the impactor 62, such as where the impactor 62 momentarily contacts the patch 72 and transfers its kinetic energy to the patch 72 (which then travels along a generally linear path that differs from the arcuate path of the impactor 62). The deployed patch 72 can be adhered to the target site, as desired for delivery of molecules.

Figure 6A:
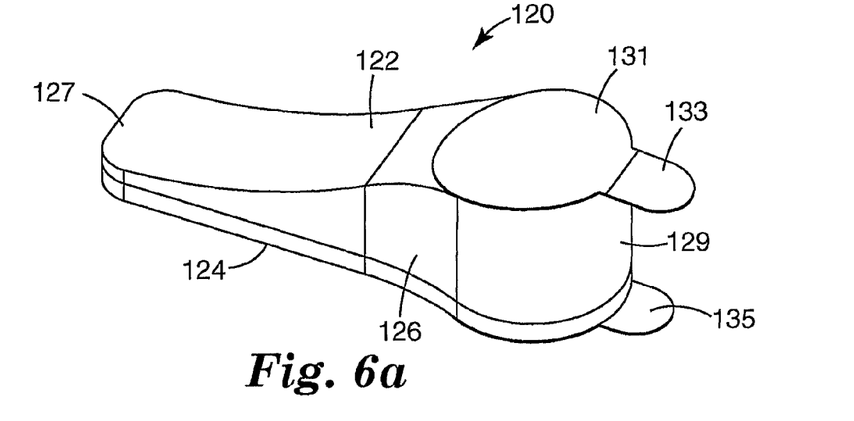
FIG. 6A is a perspective view of another applicator device having peelable seals.
Figure 6B:
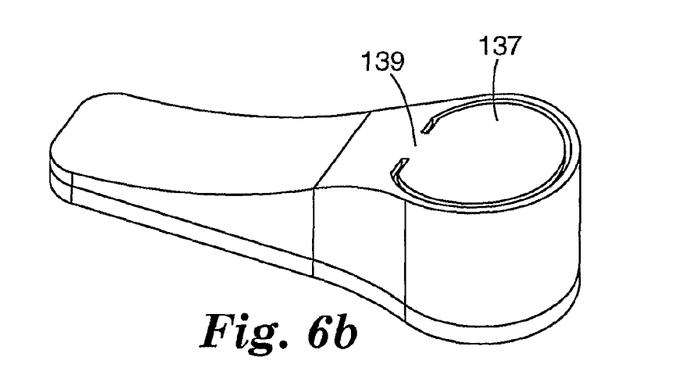
FIG. 6B is a perspective view of the applicator of FIG. 6A with the peelable seals removed.

FIG. 6A is a perspective view of another embodiment of an applicator device 120 having a housing 122 that includes a base 124 and an upper cover structure 126. The device is elongate in shape and has a first, tapered end 127 and a second end 129. The second end 129 has a top and bottom sealed by a top peelable seal 131 having a tab 133 and a bottom peelable seal 132 having a tab 135 (only tab 135 is visible in FIG. 6A). FIG. 6B shows the applicator device after the peelable seals 131, 132 have been removed. A trigger 137 is integrally formed in the top surface of the housing 122. The trigger is connected to the top surface of the housing at a single attachment point 139, thus allowing the trigger to be deflected downward by thumb or finger pressure as shown in FIG. 6D.

Figure 6C:
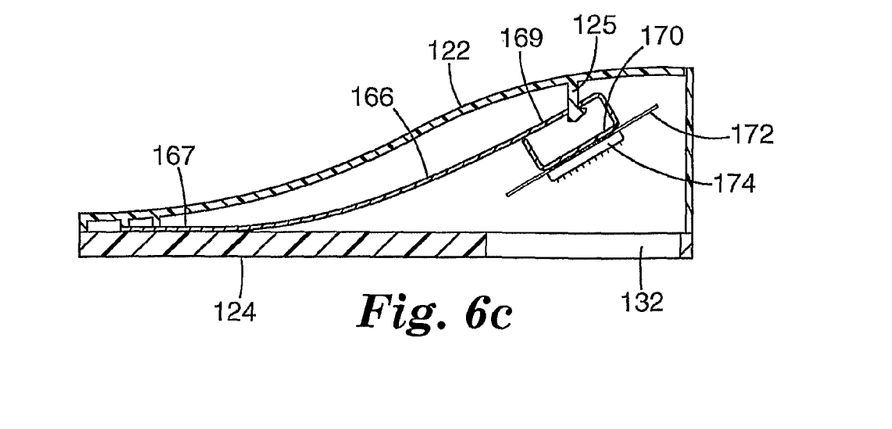
FIG. 6C is a cross-sectional view of the applicator of FIGS. 6A, B in a loaded position.
Figure 6D:
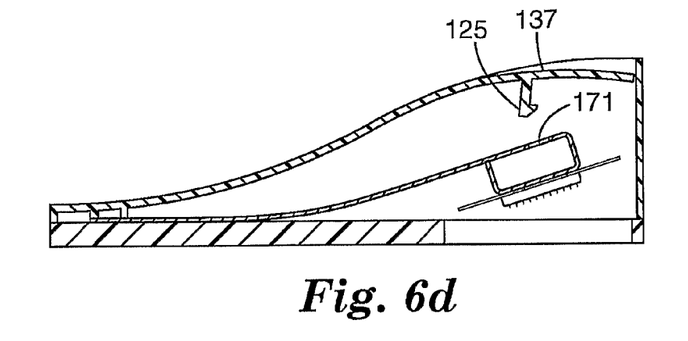
FIG. 6D is a cross-sectional view of the applicator of FIGS. 6A, B in a partially released position.
Figure 6E:
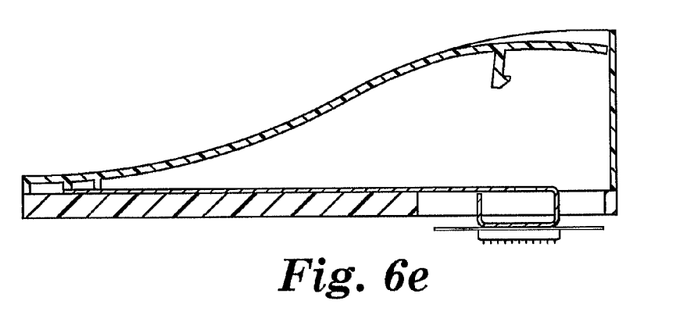
FIG. 6E is a cross-sectional view of the applicator of FIGS. 6A, B in a position where a microneedle array can contact a target surface.
Figure 6F:
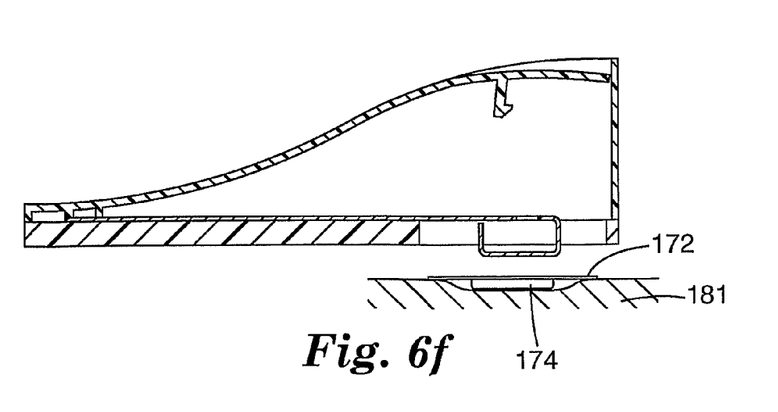
FIG. 6F is a cross-sectional view of the applicator of FIGS. 6A, B being removed from a microneedle array that has been deployed onto a target surface.

FIG. 6C is a cross-sectional view of the device showing a patch 172 mounted on an impactor 170. The impactor 170 is integrally formed with a drive member 166 having a length extending from a fixed end 167 attached to the housing 122 to a movable end 169. The drive member 166 is bendable along its length. A holding mechanism in the form of a latch uses a hook 125 attached to the housing 122. The hook 125 engages with a slot 171 in the movable end 169 of the drive member 166 to hold the movable end 169 of the drive member 166 away from the skin-contacting face 124 of the housing 122. The drive member may be any elongate, bendable member, such as, for example, a leaf spring. In use the device as shown in FIG. 6C is placed against a target surface, such as a skin surface (not shown). Depression of the trigger 137, as shown in FIG. 6D, causes the hook 125 to pivot, thus releasing the movable end 169 of the drive member 166 and allowing the drive member 166 to bias the patch 172 towards the skin-contacting face 124. FIG. 6E shows the drive member 166 fully deployed, having propelled the patch 172 past the skin-contacting face 124 so that the patch is pressed against the skin surface (not shown). FIG. 6F shows the device 120 being removed from the skin surface 181, leaving a patch 172 with a microneedle array 174 in place on the skin surface 181. As shown, the impactor 170 is shown as a curled end of a leaf spring, as this allows for a convenient means for providing a holding mechanism (via the slot 171 in the movable end 169 of the leaf spring) while also providing a separate patch contacting and holding surface. However, any variety of suitable shapes may be used for the movable end 169 of the drive member 166, including a flat leaf spring having no curled end.

Figure 7A:
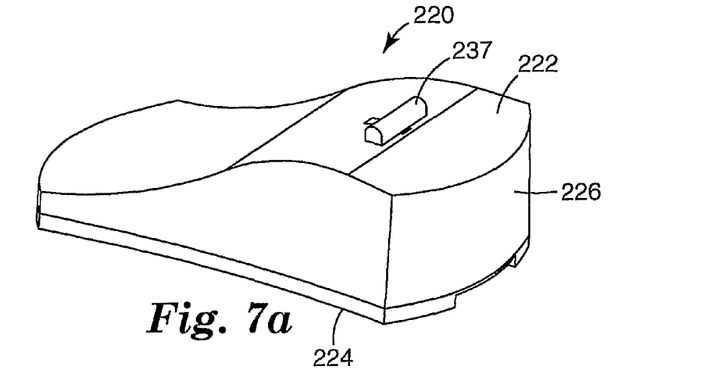
FIG. 7A is perspective top view of still another applicator device.
Figure 7B:
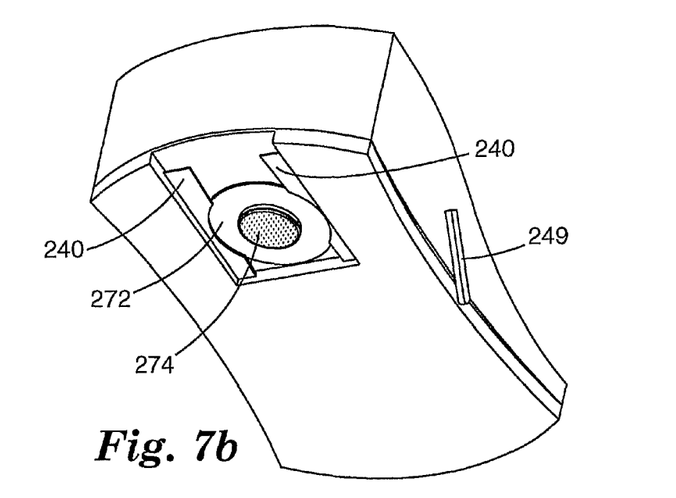
FIG. 7B is perspective bottom view of the applicator of FIG. 7A.
Figure 7C:
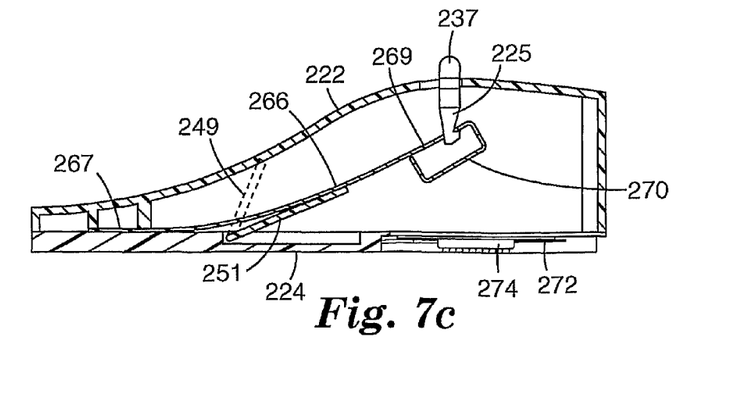
FIG. 7C is a cross-sectional view of the applicator of FIGS. 7A, B in a loaded position.
Figure 7D:
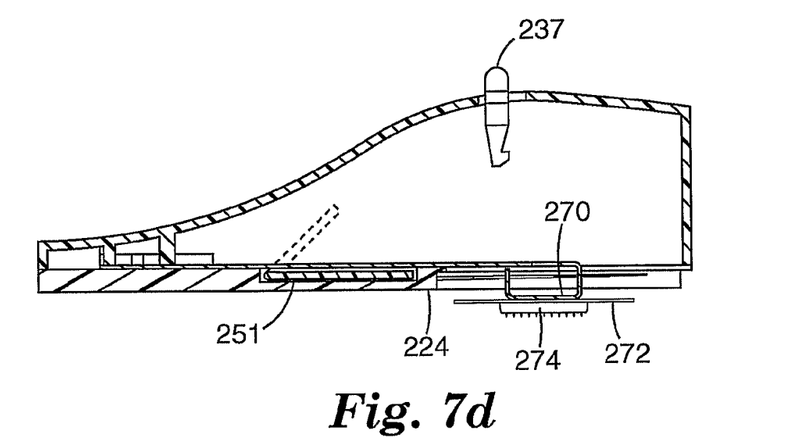
FIG. 7D is a cross-sectional view of the applicator of FIGS. 7A, B in a position where a microneedle array can contact a target surface.
Figure 7E:
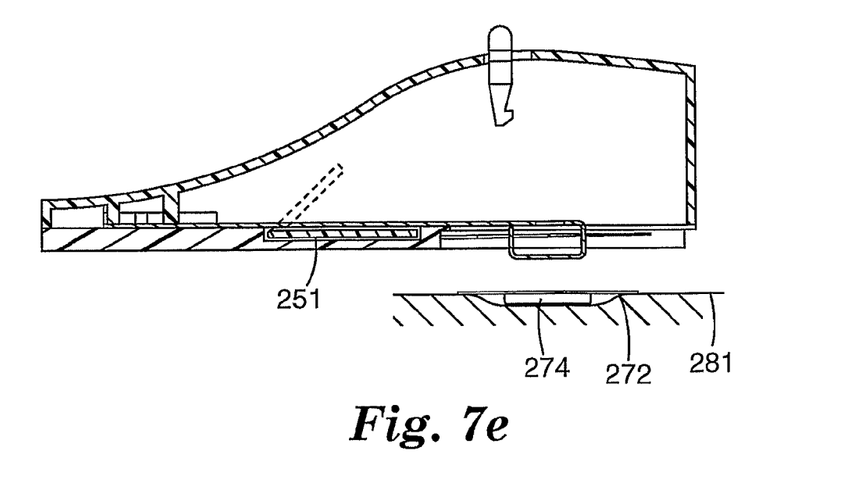
FIG. 7E is a cross-sectional view of the applicator of FIGS. 7A, B being removed from a microneedle array that has been deployed onto a target surface.

FIG. 7A is a perspective top view of another embodiment of an applicator device 220 having a housing 222 that includes a base 224 and an upper cover structure 226. A trigger 237 extends from the upper cover structure 226. FIG. 7B is perspective bottom view of the applicator 220 showing a handle 249 and having retainers 240 for holding a microneedle patch 272 with a microneedle array 274, similar to the patch retaining structure shown in FIG. 3. FIG. 7C is a cross-sectional view showing an impactor 270 integrally formed with a drive member 266 having a length extending from a fixed end 267 attached to the housing 222 to a movable end 269. The drive member 266 is bendable along its length. A holding mechanism in the form of a latch uses a hook 225 attached to the housing 222. The hook 225 engages with a slot 271 in the movable end 269 of the drive member 266 to hold the movable end 269 of the drive member 266 away from the skin-contacting face 224 of the housing 222. A lifting mechanism 251 is shown in a raised position. The lifting mechanism 251 is operably connected to the handle 249 (shown in dashed lines on the back side of the applicator) and is also configured so that it can lift the drive member 266 into a position such as shown in FIG. 7C, where the drive member 266 has been raised and latched onto hook 225. In use the device as shown in FIG. 7C is placed against a target surface, such as a skin surface (not shown). After the drive member 266 is locked in place by the holding mechanism, the handle 249 may be released, thereby releasing the lifting mechanism 251 to a lowered position, such as shown in FIG. 7D. The trigger 237 may be pushed sideways, as shown in FIG. 7D, thus releasing the movable end 269 of the drive member 266 and allowing the drive member 266 to bias the impactor 270 towards the patch 272 and the skin-contacting face 224. As shown in FIG. 7D, the impactor 270 drives the patch 272 from the retainers 240 and past the skin-contacting face 224 so that the patch is pressed against the skin surface (not shown). FIG. 7E shows the device 220 being removed from the skin surface 281, leaving a patch 272 with a microneedle array 274 in place on the skin surface 281.

The applicator 220 may be used for applying multiple patches in the following manner. After application of a patch, the handle 249 may be lifted, thereby raising the lifting mechanism 251 and thus the drive member 266 to a raised position, such as shown in FIG. 7C, and the trigger 237 may be pushed back into place to lock the drive member 266 in a raised position. The trigger 237 may be manually moved into position to lock the drive member 266. Alternatively, the trigger 237 may be moved into position to lock the drive member 266 by a spring (not shown) that biases it towards the locked position or by a mechanism (not shown) connected to the handle 249 which causes the trigger 237 to move to the locked position as the drive member 266 is raised by the handle. Any other suitable triggers and re-cocking mechanisms may be employed. Another patch may then be loaded into the retaining mechanism and applied as described above.

The applicator device of the present invention may provide numerous benefits and advantages. The housing may be shaped in a way that generally resembles a mouse for a personal computer. This shape is less threatening to patients than applicators or other drug delivery devices that are shaped, for example, like a gun. The housing also provides adequate interior volume for protecting the patch accelerating assembly and can optionally provide storage space for patches prior to application. Patch mounting may be quickly and easily accomplished, which is helpful for mass inoculations and other applications. It should be understood, however, that any suitable housing shape may be used. For example, the housing may have a circular, square, or rectangular cross-section in some embodiments and may be a polyhedron in certain embodiments (i.e., the housing may define a volume formed by plane faces). In some embodiments the housing may be a polyhedron having one or more rectangular faces, that is, a rectangular polyhedron. In some embodiments, the housing may have a flat or planar base with sides that are continuously curved. It is preferred, but not necessary, that the patch accelerating assembly is fully contained (with the exception of the handle) within the housing. In addition, a torsion spring or leaf spring allows for simple and efficient adjustment of force used to apply patch with the applicator device, permitting the applicator device to be used in a variety of contexts and for patch application to a variety of desired patch sites. A method of applying a microneedle array using an application device of the present invention comprises mounting the microneedle array on the microneedle array application device and moving the microneedle array toward the target site along a substantially arcuate path. The array, for example, may be affixed to an impactor within the device, as described above. Release of the impactor allows the array to travel towards the target site along a substantially arcuate path.

Alternatively, a method of applying a microneedle array using an application device of the present invention comprises mounting the microneedle array on the microneedle array application device and moving the impactor along a substantially arcuate path to bring the microneedle array into contact with the target site. For example, the array may be mounted within the application device using a retainer separate from the impactor, such as shown in FIG. 3, and the impactor may be placed in a loaded position (i.e., where it contains stored energy) and then released so as to travel along an arcuate path. The impactor will then contact the microneedle array (or a patch holding the microneedle array) and bring the microneedle array into contact with the target site.

In still another alternative, a method of applying a microneedle array using an application device of the present invention comprises placing a microneedle patch on or adjacent to a target site. An application device of the present invention may be brought into alignment with the microneedle array and triggered so as to cause the impactor to press the microneedle array into the target site. The microneedle patch may be held in place on a skin surface prior to contacting it with the application device by any suitable means, such as with use of a collapsible patch as described in U.S. Patent Application Ser. No. 60/693,901, filed on Jun. 24, 2005, the disclosure of which is herein incorporated by reference.

A method of applying a microneedle array using an application device of the present invention involves having the microneedle array reach a desired velocity that is effective to pierce the microneedles into the skin. The desired velocity is preferably controlled to limit or prevent stimulation of the underlying nerve tissue. The maximum velocity achieved by the microneedle array upon impact with the skin is often 20 meters per second (m/s) or less, potentially 15 m/s or less, and possibly 10 m/s or less. In some instances, the maximum velocity is 8 m/s or less. In other instances, the minimum velocity achieved by the microneedle array upon impact with the skin is often 2 m/s or more, potentially 4 m/s or more, and possibly 6 m/s or more.

The mass of the portion of the device driving the microneedle array into the skin is preferably light enough to avoid causing undue discomfort to a patient. In some instances, the mass of the impactor is less than about 6 grams, potentially less than about 4 grams, and possibly less than about 2 grams. The mass of the impactor is typically more than about 0.4 grams, potentially more than about 0.8 grams, and possibly greater than about 1.2 gram. For purposes of determining the mass of the impactor in embodiments where the impactor is integrally formed with the drive member, such as shown in FIG. 6C, the impactor will generally be considered to include the portion above and behind the microneedle array, but not to include the portion of the drive member extending away from the movable end of the drive member and towards the fixed end of the drive member.

In one embodiment, the velocity achieved by the microneedle array upon impact with the skin will be between about 4 m/s and 8 m/s, and the mass of the impactor will be between about 0.4 grams and about 2 grams. Use of a leaf spring as a drive member directly coupled to a microneedle patch may be particularly advantageous, as this allows the device to obtain desired velocities upon impact with the skin in combination with a relatively low mass impactor.

Such high-speed, low-mass delivery may be particularly advantageous when applying a microneedle array having a large number of microneedles. While not wishing to be bound by theory, it is believed that the momentum of an array having a large number of microneedles can be quite low and still achieve acceptable penetration of the microneedles through the stratum corneum, because each microneedle has a very tiny mass and only penetrates a relatively short distance into the skin. In particular, insertion of microneedle arrays having more than 100 microneedles, often more than 500 microneedles, and occasionally more than 1000 microneedles may be particularly effective when performed using devices as described above.

The depth of penetration of the microneedles will vary depending on a number of factors, such as the size and design of both the microneedles and the microneedle array, as well as upon the velocity with which the array impacts the skin. In one embodiment, the microneedles will penetrate to a depth of more than 40 µm, sometimes more than 80 µm, and occasionally more than 100 µm. In one embodiment, the microneedles will penetrate to a depth of less than 300 µm, sometimes less than 200 µm, and occasionally less than 150 µm. In another embodiment, the microneedles will penetrate to a depth that is more than 20% of the full height of the microneedle, sometimes more than 40%, and occasionally more than 50%. In another embodiment, the microneedles will penetrate to a depth that is less than about 80% of the full height of the microneedle, sometimes less than 60%, and occasionally less than 50%.

The microneedles are typically less than 500 microns in height, and sometimes less than 300 microns in height. The microneedles are typically more than 20 microns in height, often more than 50 microns in height, and sometimes more than microns in height. The height of the microneedles may be measured as the distance that they protrude from a flat base or substrate. In one embodiment, the microneedles may protrude from an irregular substrate, for example, each microneedle may rest upon a flat base or pedestal that itself protrudes from a planar substrate.

Because of the variability in the location of skin and the size of different individual's appendages, it is optional that the application device be designed such that the microneedle array travels at a velocity at or above the desired minimum velocities over a distance that is sufficient to accommodate the variations in skin location and appendage size relative to the application device. For example, the microneedle array in the application device may move at or above the minimum velocity over a distance of one millimeter or more. In some embodiments, the microneedle array may move at or above the minimum velocity over a distance of 5 millimeters or more.

The microneedle arrays useful in the various embodiments of the invention may comprise any of a variety of configurations, such as those described in the following patents and patent applications, the disclosures of which are herein incorporated by reference. One embodiment for the microneedle arrays comprises the structures disclosed in United States Patent Application Publication No. 2003/0045837. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. Another embodiment for the microneedle arrays comprises the structures disclosed U.S. Patent Application Publication No. 2005/0261631, which describes microneedles having a truncated tapered shape and a controlled aspect ratio. Still another embodiment for the microneedle arrays comprises the structures disclosed in U.S. Pat. No. 6,091,975 (Daddona, et al.) which describes blade-like microprotrusions for piercing the skin. Still another embodiment for the microneedle devices comprises the structures disclosed in U.S. Pat. No. 6,312,212 (Sherman, et al.) which describes tapered structures having a hollow central channel. Still another embodiment for the micro arrays comprises the structures disclosed in U.S. Pat. No. 6,379,324 (Gartstein, et al.) which describes hollow microneedles having at least one longitudinal blade at the top surface of tip of the microneedle.

Microneedle arrays and microneedle patches of the present invention may be used to deliver drugs (including any pharmacological agent or agents) through the skin in a variation on transdermal delivery, or to the skin for intradermal or topical treatment, such as vaccination.

In one aspect, drugs that are of a large molecular weight may be delivered transdermally. Increasing molecular weight of a drug typically causes a decrease in unassisted transdermal delivery. Microneedle arrays of the present invention have utility for the delivery of large molecules that are ordinarily difficult to deliver by passive transdermal delivery. Examples of such large molecules include proteins, peptides, nucleotide sequences, monoclonal antibodies, DNA vaccines, polysaccharides, such as heparin, and antibiotics, such as ceftriaxone.

In another aspect, microneedle arrays and microneedle patches of the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamedronate; and molecules with physicochemical properties that are not conducive to passive transdermal delivery.

In another aspect, microneedle arrays and microneedle patches of the present invention may have utility for enhancing delivery of molecules to the skin, such as in dermatological treatments, vaccine delivery, or in enhancing immune response of vaccine adjuvants.

Microneedle arrays and microneedle patches may be used for immediate delivery, that is where they are applied and immediately removed from the application site, or they may be left in place for an extended time, which may range from a few minutes to as long as 1 week. In one aspect, an extended time of delivery may be from 1 to 30 minutes to allow for more complete delivery of a drug than can be obtained upon application and immediate removal. In another aspect, an extended time of delivery may be from 4 hours to 1 week to provide for a sustained release of drug.

Although the present invention has been described with reference to several alternative embodiments, workers skilled in the art will recognize that changes may be made in form and detail without departing from the spirit and scope of the invention.

The invention claimed is:

1. An application device for applying a microneedle array comprising:
   a housing having a skin-contacting face defining an opening that can be positioned at a target site;
   an impactor for impacting the microneedle array and accelerating the microneedle array toward the target site, wherein the impactor is capable of moving along a substantially arcuate path to move the microneedle array along an arcuate path toward the opening of the skin-contacting face of the housing; and
   a drive member for biasing the impactor relative to the housing, wherein the drive member has a length extending from a fixed end attached to the housing to a movable end, wherein the drive member is bendable deflectable, relative to the housing, along the length of the drive member, wherein the movable end of the drive member is configured so as to be able to contact and propel the microneedle array and wherein the microneedle array is affixed to the movable end of the drive member.

2. The application device as claimed in claim 1, and further comprising a first retainer disposed along and spaced from the skin-contacting face of the housing and adjacent to the opening.

3. The application device as claimed in claim 2, wherein the first retainer has a release surface.

4. The application device as claimed in claim 3, wherein the release surface faces the housing.

5. The application device as claimed in claim 2, wherein the first retainer has a release coating applied thereon.

6. The application device as claimed in claim 2, and further comprising a second retainer disposed along and spaced from the skin-contacting face of the housing and adjacent to the opening.

7. The application device of claim 1, and further comprising a recess along the skin-contacting face, wherein the opening is disposed in the recess.

8. The application device of claim 1, and further comprising an actuation protrusion connected to the impactor for allowing an operator to manually position the impactor along the substantially arcuate path.

9. The application device of claim 1, wherein the opening includes a wider portion for passage of a microneedle array therethrough.

10. The application device of claim 1, wherein an acceleration rate of the microneedle array toward the target site is adjustable.

11. The application device of claim 1, wherein the microneedle array moves along an at least partially arcuate path toward the target site.

12. The application device as claimed in claim 1, wherein the movable end of the drive member serves as the impactor.

13. The application device as claimed in claim 1 and further comprising a holding mechanism for holding the movable end of the drive member away from the skin-contacting face of the housing.

14. The application device as claimed in claim 13 and further comprising a trigger for releasing the movable end of the drive member from the holding mechanism.

15. The application device as claimed in claim 1 wherein the drive member comprises a leaf spring.

16. An application device for applying a microneedle array comprising:
   a housing having a skin-contacting face defining an opening that can be positioned at a target site;
   an impactor for impacting the microneedle array and accelerating the microneedle array toward the target site, wherein the impactor is capable of moving along a substantially arcuate path to move the microneedle array along an arcuate path toward the opening of the skin-contacting face of the housing; and
   a drive member for biasing the impactor relative to the housing, wherein the drive member has a length extending from a fixed end attached to the housing to a movable end, wherein the drive member is bendably deflectable, relative to the housing, along the length of the drive member, wherein the movable end of the drive member is configured so as to be able to contact and propel the microneedle array, and
   wherein the microneedle array is releasably affixed to the movable end of the drive member.

17. The application device of claim 1, and further comprising:
   a torsion spring for biasing the impactor relative to the housing.

18. The application device as claimed in claim 17, wherein a first position and a second position are defined along the substantially arcuate path, and wherein potential energy stored in the torsion spring when the impactor is positioned relative to the first position differs from when the impactor is positioned relative to the second position.

* * * * *

UNITED STATES PATENT AND TRADEMARK OFFICE
CERTIFICATE OF CORRECTION

| | | |
|---|---|---|
| PATENT NO. | : 8,784,363 B2 | Page 1 of 1 |
| APPLICATION NO. | : 11/993137 | |
| DATED | : July 22, 2014 | |
| INVENTOR(S) | : Frank Frederickson | |

It is certified that error appears in the above-identified patent and that said Letters Patent is hereby corrected as shown below:

Specification

Column 2,
Line 34, delete "microneedle," and insert -- microneedle --, therefor.

Claims

Column 13,
Line 22, in Claim 1, delete "bendable" and insert -- bendably --, therefor.

Signed and Sealed this
Ninth Day of December, 2014

Michelle K. Lee
*Deputy Director of the United States Patent and Trademark Office*